United States Patent [19]

Neumann

[11] Patent Number: 5,105,014
[45] Date of Patent: Apr. 14, 1992

[54] SYNTHESIS OF VICINAL DIAMINES

[75] Inventor: William L. Neumann, Grover, Mo.

[73] Assignee: Mallinckrodt Medical, Inc., St. Louis, Mo.

[21] Appl. No.: 741,012

[22] Filed: Aug. 6, 1991

[51] Int. Cl.$^5$ ............................................ C07C 209/62
[52] U.S. Cl. .................................... 564/486; 522/100; 564/321; 564/370; 564/372; 564/472; 564/489
[58] Field of Search ............... 564/321, 370, 372, 472, 564/486, 489; 552/100

[56] References Cited

U.S. PATENT DOCUMENTS 4,792,631 12/1988 Mueller et al. ...................... 564/489

Primary Examiner—Richard L. Raymond
Attorney, Agent, or Firm—David A. Hey

[57] ABSTRACT

The present invention relates to an improved method of forming vicinal diamines. The method according to the present invention has the advantage of being highly stereoselective, capable of forming a wide variety of diamines including racemic and enantiomeric forms, and employing readily available starting and reaction materials.

In particular the present invention relates to a method of forming vicinal diamines from a bis-imine precursor using nucleophilic additions of organometallic reagents.

9 Claims, No Drawings

SYNTHESIS OF VICINAL DIAMINES

BACKGROUND

In recent years, vicinal diamines have been found to be useful in an uncommonly wide variety of applications. In particular, vicinal diamines play an important role in direct metal chelation. Also, vicinal diamines have been found to be a key architectural component for a wide range of natural products and also for medicinally active compounds. Therefore, studies directed toward the synthesis and preparation of vicinal diamine systems have intensified.

Rapid advances have occurred in the development of synthetic methods for preparing vicinal diamines, however, most of these new synthetic methods have the disadvantage of limited scope or limited stereoselectivity. Several recently developed synthetic methods are based upon the generation of vicinal diazides, dinitro, and other related nitrogen oxidation state equivalents, and their subsequent reduction to a corresponding diamine. These methods have several disadvantages, including the lack of stereoselectivity, susceptibility to side-reactions upon reduction, and the necessity of handling dangerous, explosive intermediates, such as azides.

Other new synthetic methods are based upon the ring opening of aziridines with ammonia or amines, or those which employ intramolecular cyclizations. These methods offer a greater degree of stereocontrol than those mentioned above, but have the disadvantage of requiring long chemical synthesis sequences in order to set up the key nitrogen installation step.

Several other synthetic methods have been developed, however, all have exhibited disadvantages. In particular, active metal mediated reductive dimerization of Schiff bases has been thoroughly examined, and has been found useful only for the preparation of aromatic secondary vicinal diamines. Further, niobium promoted coupling of nitriles or N-(trimethylsilyl)imines has been found applicable to the synthesis of primary diamines, but has the disadvantages of unpredictable stereoselectivity and requiring the use of specialized reagents. Moreover, the reductive amination of α-amino aldehydes and α-amino ketones, the reduction of α-amino amides and α-amino nitriles and the reduction of or addition to α-amino imines have all proved to be useful reaction synthesis techniques, but are greatly limited in utility because of the accessibility of suitable starting materials. Also, these techniques generally require the preliminary modification of amino acids as chiral educts in order to extend to enantioselective synthesis.

OBJECTS OF THE INVENTION

It is one object of the present invention to provide a method of producing functionalized vicinal diamines, which method is highly stereoselective.

It is another object of the present invention to provide a method of producing functionalized vicinal diamines which method is useful for a wide variety of diamines including racemic (d,l) and enantiomeric forms.

It is still another object of the present invention to provide a method of producing functionalized vicinal diamines, which method employs readily available starting and reaction materials.

SUMMARY OF THE INVENTION

The above objects and others are accomplished according to the present invention by providing a method of forming vicinal diamines from a bis-imine precursor using nucleophilic additions of organometallic reagents.

DETAILED DESCRIPTION OF THE INVENTION

The present invention relates to an improved method of forming vicinal diamines. The method according to the present invention has the advantage of being highly stereoselective, capable of forming a wide variety of diamines including racemic and enantiomeric forms, and employing readily available starting and reaction materials.

It has been discovered that desired diamine systems may be readily and selectively formed from bis-imine precursors by nucleophilic additions of organometallic reagents according to the following general reaction sequence.

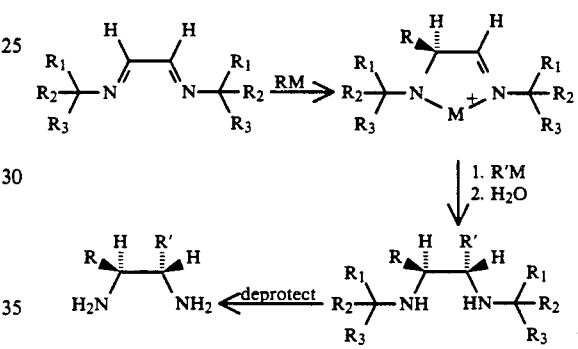

wherein $R_1$, $R_2$, and $R_3$ may be the same or different and are selected from the group consisting of hydrogen, phenyl, methyl and naphthyl, and may be in an (R) or (S) enantiomeric form;

R and R' may be the same or different and are selected from the group consisting of any alkyl, alkenyl, alkynyl, and aryl, bearing any functional group which is compatible with organo-metallic formation and reaction; and M is selected from the group consisting of Mg, MgX wherein X is a halide, Li, Cu, Ce, Zn, Si, Sn, B, Yb, La, and Cd.

The use of bis-imine precursors is advantageous in providing high stereoselectivity, as seen in the above reaction sequence (I). In particular, the first equivalent addition by reaction with an organometallic reagent provides a chelated intermediate which then directs the second equivalent addition to occur on the opposite side from the first addition.

Preferred bis-imine precursors have the general formula as shown in reaction sequence (I) wherein $R_1$, $R_2$, and $R_3$ are defined according to one of the following schemes:

(a) $R_1=R_2=$phenyl, $R_3=$hydrogen;
(b) $R_1=R_2=R_3=$phenyl;
(c) $R_1=$hydrogen, $R_2=$phenyl, $R_3=$methyl, (R)-enantiomer;
(d) $R_1=$hydrogen, $R_2=$phenyl, $R_3=$methyl, (S)-enantiomer;

(e) $R_1$=hydrogen, $R_2$=naphthyl, $R_3$=methyl, (R)-enantiomer; or (f) $R_1$=hydrogen, $R_2$=naphthyl, $R_3$=methyl, (S)-enantiomer.

The bis-imine precursors may be formed by condensation of α-substituted benzylamines with glyoxal according to the following reaction sequence.

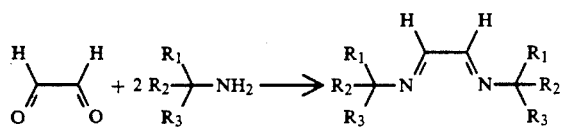

wherein $R_1$, $R_2$, and $R_3$ are defined in the same manner as for reaction sequence (I) above.

The bis-imines of glyoxal are particularly attractive precursors, because they represent the simplest possible vicinal diamine synthon. In particular, the two permanent adjacent carbon atoms of the glyoxal bis-imine will become the two adjacent carbon atoms of the desired vicinal diamine. Therefore, it is possible to form a functionalized and highly stereoselective vicinal diamine system from the two carbon atom precursor and suitably functionalized organometallic reagents in a highly convergent manner as shown in reaction sequence (I).

In addition, the use of α-substituted benzylamines in forming the bis-imine precursors is advantageous. In particular, the expendable α-substituted benzyl protecting group components may be readily cleaved from the final intermediate to generate the desired functionalized vicinal diamine, as shown in reaction sequence (I). As noted above, the protecting groups, i.e. $R_1$, $R_2$, and $R_3$ are preferably, but not limited to, diphenylmethyl (a), triphenylmethyl (b), (R)-α-methylbenzyl (c), (S)-α-methylbenzyl, (d), (R)-1-naphthylethyl (e), and (S)-1-naphthylethyl (f).

As noted above in reaction sequence (I), the organometallic reagents may contain any functional group on any protected or latent functionality which is compatible with organometallic formation and reaction with the bis-imine precursors. The metal component of the organometallic reagent can be any one that is typically used for the generation of reagents for organic synthesis methods, such as Mg, MgX wherein X is a halide, Li, Cu, Ce, Zn, Si, Sn, B, Yb, La, and Cd. In particular, magnesium, lithium and cerium have been found to work particularly well. The R and R' groups may be any alkyl, alkenyl, alkynyl, or aryl, bearing any functional group compatible with organometallic formation and reaction. The R and R' groups which are added to the bis-imine may be the same to afford symmetrical vicinal diamines, or may be different to afford unsymmetrical vicinal diamines.

The following examples and experimental results provide specific examples of the synthetic method according to the present invention, but are not intended to be limiting in any way. It will be recognized that the method according to the present invention is applicable to a wide range of applications beyond those shown in the following examples and experimental results.

EXAMPLE 1

Preparation of (d,l)-4,5-diamino-1,7-octadiene

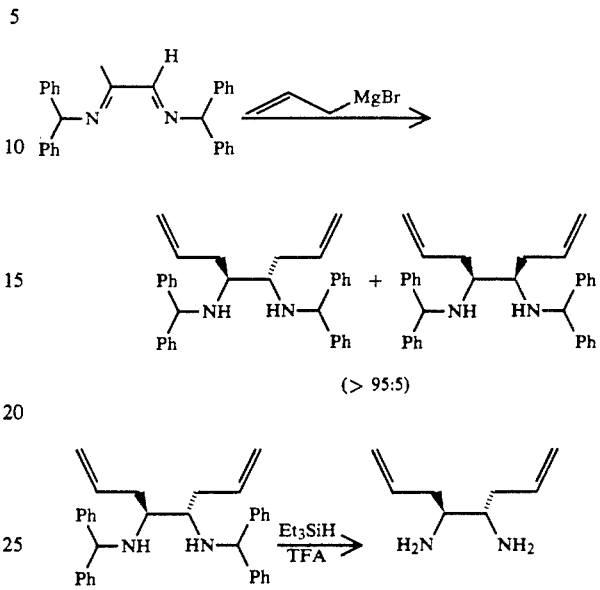

To diphenylmethyl bis-imine is added in dropwise manner, allyl magnesium bromide in tetrahydrofuran (THF) solution, to produce chelation controlled (d,l) addition product in a 95% or more yield and a non-chelation controlled (meso) isomer in 5% or less yield, as determined by NMR analysis. Higher temperatures and/or rapid addition rates of allyl magnesium bromide give higher percentage yields of the meso isomer. However, under stringent condition control, the ratio of (d,l) to meso isomers if never less than 6:1. The (d,l) isomer is then treated with an excess of triethylsilane in trifluoroacetic acid (TFA) to cleave the diphenylmethyl protecting groups and resulting in the desired functionalized (d,l)-vicinal diamine in 82% overall yield from the bis-imine.

EXAMPLE 2

Preparation of (4R,5R)- and (4S,5S)-4,5-diamino-1,7-octadiene

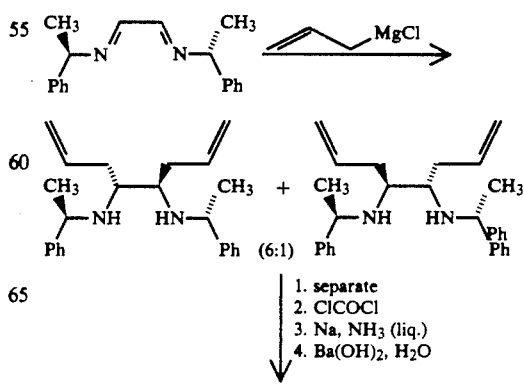

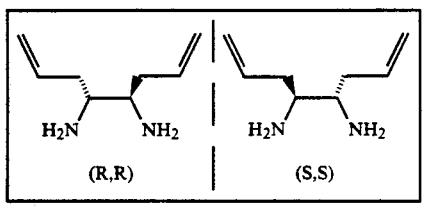

Allyl magnesium chloride is added to (R)-α-methylbenzyl bis-imine in THF solution, in the same manner as described in Example 1, to yield (R,R) and (S,S) forms of protected vicinal diamines in a 6:1 ratio. The (R,R) and (S,S) forms may then be separated by flash column chromatography and the benzylic protecting groups may be cleaved by the following sequence: conversion to the cyclic urea with phosgene (or a phosgene equivalent), dissolving metal reduction (sodium in liquid ammonia), and base hydrolysis (an excess of aqueous barium hydroxide).

EXAMPLE 3

Enantiomerically pure (R,R) and (S,S) forms of chiral diaminooctadienes as synthesized in Example 2 may also be formed using (R)-1-naphthylethyl bis-imine as the starting material. Using the same synthesis as described in Example 2, the (R,R) and (S,S) forms of the desired chiral diaminooctadienes may be formed in a ratio of 3:1.

EXAMPLE 4

Preparation of (4R,5R)- and (4S,5S)-4,5-diamino-1,7-octadiene

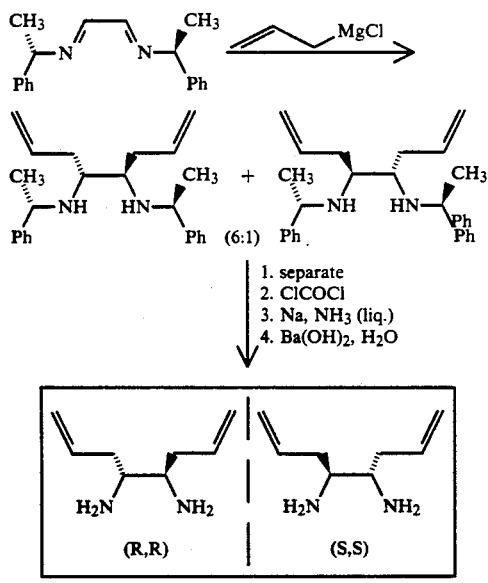

Allyl magnesium chloride is added to (S)-α-methylbenzyl bis-imine in THF solution, in the same manner as described in Example 1, to yield (R,R) and (S,S) forms of protected vicinal diamines in a 1:6 ratio. The (R,R) and (S,S) forms may then be separated by flash column chromatography and the benzylic protecting groups may be cleaved by the following sequence: conversion to the cyclic urea with phosgene (or a phosgene equivalent), dissolving metal reduction (sodium in liquid ammonia), and base hydrolysis (an excess of aqueous barium hydroxide).

EXAMPLE 5

Enantiomerically pure (R,R) and (S,S) forms of chiral diaminooctadienes as synthesized in Example 4 may also be formed using (S)-1-naphthylethyl bis-imine as the starting material. Using the same synthesis as described in Example 2, the (R,R) and (S,S) forms of the desired chiral diaminooctadienes may be formed in a ratio of 1:3.

EXAMPLE 6

Deprotection of intermediates in the preparation of chiral vicinal diamines

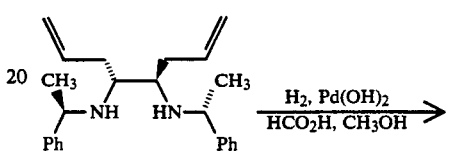

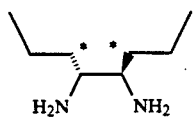

The intermediate vicinal diamines shown in Examples 2 through 5 may be deprotected and converted to the corresponding saturated vicinal diamine systems in a one step catalytic hydrogenation as shown above. In particular, the protected diamine is dissolved in methanol, treated with a catalytic amount of 20% Pd(OH)$_2$ on carbon and exposed to 1 atmosphere of hydrogen gas flow for 12 hours.

Experimental 1,1,6,6-tetraphenyl-2,5-diaza-2,4-hexadiene

To glyoxal (20 g of a 40% aqueous solution, 138 mmol) was added hexanes (50 ml) and the mixture was stirred vigorously. Diphenylmethylamine (47.5 ml, 276 mmol) was added dropwise and the resulting mixture was stirred for 2 hours and filtered. The filter-cake was washed well with methanol and dried at high vacuum to afford 50.6 g (95%) of 1,1,6,6-tetraphenyl-2,5-diaza-2,4-hexadiene as a white powder. $^1$H NMR (CDCl$_3$):d 8.21 (s, 2 H), 7.20–7.37 (m, 20 H), 5.59 (s, 2 H). $^{13}$C NMR (CDCl$_3$):d 162.4 (d), 142.8 (s), 128.7 (d), 127.5 (d), 78.0 (d).

(d,l)-4,5-bis(diphenylmethylamino)octa-1,7-diene

To diphenylmethyl bis-imine (50.0 g, 129 mmol) in THF (200 ml) at −78° C. was added dropwise allylmagnesium bromide (284 ml of a 1.0M solution in ether, 284 mmol) over a 3 hour period. This mixture was allowed to warm to room temperature and stir over night. The mixture was recooled to 0° C. and quenched with the dropwise addition of water (200 ml) and saturated NH$_4$OH (200 ml). The layers were separated and the aqueous was extracted with ether (3×100 ml). The combined organics were dried (Na$_2$SO$_4$) and concentrated thoroughly to afford 57 g (93%) of (d,l)-4,5-bis(-diphenylmethylamino)octa-1,7-diene as a single diastereomer by NMR. $^1$H NMR (CDCl$_3$):d 7.15–7.50 (m, 20 H), 5.55–5.71 (m, 2 H), 4.88–5.02(m, 4 H), 2.69 (app t, J=5 Hz, 2 H), 2.46-2.58 (m, 2 H), 2.15-2.25 (m, 2 H), 1.82 (bs, 2 H). $^{13}$C NMR (CDCl$_3$):d 145.4 (s), 145.1 (s), 137.2 (d), 129.1 (d), 128.9 (d), 128.4 (d), 128.1 (d), 127.6 (d), 127.5 (d), 117.5 (t), 54.1 (d), 56.6 (d), 35.1 (t).

4,5-diamino-1,7-octadiene

To protected (d,l)-4,5-bis(diphenylmethylamino)octa-1,7-diene (56.6 g, 120 mmol) in TFA (100 ml) was added triethyl silane (57.4 ml, 360 mmol) and the mixture was heated to reflux for 2 hours. At this time the reaction flask was fitted with a short-path distillation head and nearly all the TFA was distilled off. The residue was allowed to cool, diluted with water (100 ml), and washed with ether (3×100 ml). The aqueous portion was cooled to 10° C., made basic with solid KOH, and extracted with CH$_2$Cl$_2$ (6×100 ml). The combined extracts were dried (Na$_2$SO$_4$) and concentrated. Fractional distillation of the residue (68° C. @ 2.5 mm Hg) afforded 7.70 g (46%) of pure 4,5-diamino-1,7-octadiene as a slightly yellow liquid. $^1$H NMR (CDCl$_3$):d 5 65-5.81 (m, 2 H), 4.98-5.10 (m, 4 H), 2.55-2.65 (m, 2 H), 1.95-2.29 (m, 4 H), 1.26 (bs, 4 H). $^{13}$C NMR (CDCl$_3$):d 136.5 (d), 117.9 (t), 54.6 (d), 39.8 (t). MS (HREI) m/z=139.1232 (m−1) (139.1235 calculated for C$_8$H$_{15}$N$_2$).

(4R, 5R)-bis-[(R)-1-phenylethylamino]-1,7-octadiene

To (R)-α-methylbenzyl bis-imine (4.16 g, 15.7 mmol) in THF (30 ml) at −78° C. was added allyl magnesium bromide (35.0 ml of a 1.0M solution in ether, 35.0 mmol) dropwise over 1 hour. The resulting mixture was allowed to warm to room temperature gradually and stir over night. The reaction mixture was cooled to 10° C. and quenched with 15% NH$_4$Cl (50 ml). The resulting mixture was extracted with ether (3×150 ml), dried (K$_2$CO$_3$—Na$_2$SO$_4$):, filtered and concentrated to afford a 2.3:1 mixture (by NMR) of chelation controlled addition products. Filtration through a short plug of silica gel with Et$_2$O and concentration afforded 5.20 g (95%) of the pure mixture of diastereomers. Separation by flash column chromatography (SiO$_2$, 9:1 Hexane - EtOac) afforded 3.30 g (70%) of (4R, 5R)-bis-[(R)-1-phenylethylamino]-1,7-octadiene as a white solid. [a]$^{19.5}$=+121.9° (26.5 mg/ml CH$_2$Cl$_2$). $^1$H NMR (CDCl$_3$):d 7.18-7.30 (m, 10 H), 5.40 (m, 2 H), 4.76 (dd, J=10.2 Hz, 16.0 Hz, 4 H), 3.75 (q, J=6.6 Hz, 2 H), 2.17 (m, 2 H), 2.00-2.26 (m, 4 H), 1.28 (d, 6.6 Hz). $^{13}$C NMR (CDCl$_3$):d 146.6 (s), 136.6 (d), 128.3 (d), 127.3 (d), 126.9 (d), 116.5 (t), 56.4 (d), 55.9 (d), 34.7 (t), 24.9 (q). Analytically calculated for C$_{24}$H$_{32}$N: C, 82.70; H, 9.26; N, 8.04. Found: C, 82.71; H, 9.26; N, 8.00.

(4S, 5S)-bis-[(R)-1-phenylethylamino]-1,7-octadiene, 1.42 g (30%) as a mobile colorless oil was isolated from a slightly higher rf fraction: [a]$^{19.5}$=+35.0° (23.6 mg/ml CH$_2$Cl$_2$). $^1$H NMR (CDCl$_3$):d 7.11-7.35 (m, 10 H), 5.68 (m, 2 H), 5.05 (d, J=12.2 Hz, 4 H), 2.58 (m, 2 H), 2.41 (m, 2 H), 1.91 (m, 2 H), 1.39 (bs, 2 H), 3.62 (q, J=6.5 Hz, 2 H), 1.19 (d, J=6.5 Hz, 6 H). $^{13}$C NMR (CDCl$_3$):d 146.6 (s), 137.4 (d), 128.4 (d), 126.8 (d), 116.9 (t), 55.2 (d), 54.6 (d), 34.5 (t), 24.5 (q). Analytically calculated for C$_{24}$FH$_{32}$N$_2$: C, 82.70; H, 9.26; N, 8.04. Found: C, 82.64; H, 9.23; N, 8.04.

(4S, 5S)-bis-[(S)-1-phenylethylamino]-1,7-octadiene

Prepared from (S)-α-methylbenzyl bis-imine (800 mg, 3.00 mmol) and allyl magnesium chloride (7.6 ml or a 1.0M solution in THF, 7.6 mmol) by the same procedure used for the preparation of (4R, 5R)-bis-[(R)-1-phenylethylamino]-1,7-octadiene above, afforded a 2.4:1 (by NMR) mixture of the (R,R) and (S,S) forms of protected vicinal diamines as noted in Example 4 above. Separation of flash column chromatography (9:1 hexane-EtOAc) afforded 510 mg of the S,S form of protected vicinal diamine as a white solid: [a]$^{19.5}$=122.0° (28.0 mg/ml CH$_2$Cl$_2$). This material afforded NMR spectra which are identical in all respects to those of its enantiomer (4R, 5R)-bis-[(R)-1-phenylethylamino]-1,7-octadiene. (4R, 5R)-bis-[(S)-1-phenylethylamino]-1,7-octadiene was isolated as a slightly higher rf fraction, 213 mg of a colorless oil: [a]$^{19.5}$=−34.0° (15.1 mg/ml CH$_2$Cl$_2$). This material affords NMR spectra which are identical in all respects to those of its enantiomer (4S, 5S)-bis-[(R)-1-phenylethylamino]-1,7-octadiene.

(4R, 5R)-4,5-diaminooctane

Compound (4R, 5R)-bis-[(R)-1-phenylethylamino]-1,7-octadiene (240 mg, 0.69 mmol) was dissolved in methanol (5 ml) and treated with 20% Pd (OH)$_2$/C (30 mg) and 1 drop 80% aqueous formic acid. Hydrogen was bubbled over the stirred solution (continuous flow) for 12 hours. Filtration and concentration afforded 100 mg (100%) of pure chiral diamine (4R, 5R)-4,5-diaminooctane: [a]$^{19.5}$=14.5°. $^{13}$C-NMR CD$_2$OD): d 53.6 (d), 30.2 (t), 19.7 (t), 13.9 (q).

The foregoing has been a description of certain preferred embodiments of the present invention, but is not intended to limit the invention in any way. Rather, many modifications, variations and changes in details may be made within the scope of the present invention.

What is claimed is:

1. A method of forming vicinal diamines from bis-imine precursors by nucleophilic additions of organo-metallic reagents wherein said method follows the reaction sequence

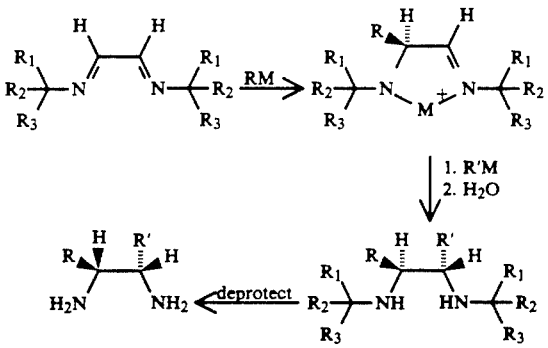

wherein

R$_1$, R$_2$, and R$_3$ may be the same or different and are selected from the group consisting of hydrogen, phenyl, methyl and naphthyl, and may be in an (R) or (S) enantiomeric form;

R and R' may be the same or different and are selected from the group consisting of any alkyl, alkenyl, alkynyl, and aryl, bearing any functional group which is compatible with organo-metallic formation and reaction; and M is selected from the group consisting of Mg, MgX wherein X is a halide, Li, Cu, Ce, Zn, Si, Sn, B, Yb, La, and Cd.

2. A method according to claim 1, wherein R$_1$ and R$_2$ are phenyl groups, and R$_3$ is hydrogen.

3. A method according to claim 1, wherein $R_1$, $R_2$ and $R_3$ are phenyl groups.

4. A method according to claim 1, wherein $R_1$ is hydrogen, $R_2$ is a phenyl group, and $R_3$ is a methyl group, and wherein said precursor bis-imine has an (R)-enantiomeric form.

5. A method according to claim 1, wherein $R_1$ is hydrogen, $R_2$ is a phenyl group, and $R_3$ is a methyl group, and wherein said precursor bis-imine has an (S)-enantiomeric form.

6. A method according to claim 1, wherein $R_1$ is hydrogen, $R_2$ is a naphthyl group, and $R_3$ is a methyl group, and wherein said precursor bis-imine has an (R)-enantiomeric form.

7. A method according to claim 1, wherein $R_1$ is hydrogen, $R_2$ is a naphthyl group, and $R_3$ is a methyl group, and wherein said precursor bis-imine has an (S)-enantiomeric form.

8. A method according to claim 1, wherein said precursor bis-imine is formed by condensation of α-substituted benzylamines with glyoxal according to the following reaction sequence
wherein $R_1$, $R_2$, and $R_3$ may be the same or different and are selected from the group consisting of hydrogen, phenyl, methyl and naphthyl, and may be in an (R) or (S) enantiomeric form.

9. A method according to claim 1, wherein M is selected from the group consisting of magnesium, lithium and cerium.

* * * * *